(12) United States Patent
Wysocki et al.

(10) Patent No.: US 9,678,044 B2
(45) Date of Patent: Jun. 13, 2017

(54) METHOD OF MEASURING ACOUSTIC ENERGY IMPINGING UPON A CABLE

(71) Applicants: Paul F. Wysocki, Blacksburg, VA (US); Ian Mitchell, Radford, VA (US); Matthew Thomas Raum, Blacksburg, VA (US)

(72) Inventors: Paul F. Wysocki, Blacksburg, VA (US); Ian Mitchell, Radford, VA (US); Matthew Thomas Raum, Blacksburg, VA (US)

(73) Assignee: BAKER HUGHES INCORPORATED, Houston, TX (US)

( * ) Notice: Subject to any disclaimer, the term of this patent is extended or adjusted under 35 U.S.C. 154(b) by 168 days.

(21) Appl. No.: 14/661,364

(22) Filed: Mar. 18, 2015

(65) Prior Publication Data

US 2016/0274064 A1    Sep. 22, 2016

(51) Int. Cl.
*G01N 29/24*    (2006.01)

(52) U.S. Cl.
CPC .................................. *G01N 29/2418* (2013.01)

(58) Field of Classification Search
CPC .................................................. G01N 29/2418
USPC ........................................................... 73/655
See application file for complete search history.

(56) References Cited

U.S. PATENT DOCUMENTS

| | | | | |
|---|---|---|---|---|
| 5,479,553 | A * | 12/1995 | Daems | G02B 6/4446 385/135 |
| 5,929,341 | A * | 7/1999 | Bawden | E21D 21/02 73/152.59 |
| 6,856,401 | B1 * | 2/2005 | Rønnekleiv | G01D 5/344 356/477 |
| 2006/0232869 | A1 * | 10/2006 | Itagi | G11B 5/1872 360/59 |
| 2008/0088846 | A1 | 4/2008 | Hayward et al. | |
| 2009/0157358 | A1 * | 6/2009 | Kim | G01L 1/16 702/185 |
| 2009/0220187 | A1 | 9/2009 | Goldner et al. | |
| 2009/0274456 | A1 | 11/2009 | Healey et al. | |
| 2011/0007996 | A1 | 1/2011 | Huffman | |
| 2012/0020631 | A1 | 1/2012 | Rinzler et al. | |
| 2016/0161631 | A1 * | 6/2016 | Jaaskelainen | E21B 47/00 356/72 |
| 2016/0266265 | A1 * | 9/2016 | Kruspe | G01V 1/186 |

OTHER PUBLICATIONS

International Search Report and Written Opinion of the International Searching Authority, or the Declaration for International Applicaiton No. PCT/US2016/018465, Issued May 12, 2016, 12 pages.

\* cited by examiner

*Primary Examiner* — J M Saint Surin
(74) *Attorney, Agent, or Firm* — Cantor Colburn LLP

(57) ABSTRACT

A method of measuring acoustic energy impinging upon a cable includes, interrogating at least one optical fiber of the cable with electromagnetic energy, the at least one optical fiber is nonconcentrically surrounded by and strain locked to a sheath of the cable, monitoring electromagnetic energy returned in the at least one optical fiber, and determining acoustic energy impinging on the cable.

19 Claims, 2 Drawing Sheets

METHOD OF MEASURING ACOUSTIC ENERGY IMPINGING UPON A CABLE

BACKGROUND

Conventional distributed acoustic sensing (DAS) systems rely on the coupling of energy in propagating seismic waves into longitudinal vibrational modes of the fiber (i.e. vibrations of the fiber that are parallel to the axis of the fiber). Typical DAS interrogators send coherent laser pulses into a fiber and measure the Rayleigh backscattered light from those pulses as a function of time (which is then mapped to fiber position). Backscatter from distinct points within the region illuminated by the pulse as it propagates through the fiber interfere and therefore the phase and amplitude of backscatter power received from any given region (corresponding to a pulse width) is very sensitive to the distance between the points in the region where backscatter occurs. Acoustic signals that create longitudinal vibrations in the fiber are detected as variations in the backscattered power from any given region of the fiber as successive laser pulses are sent and the backscatter signals measured as a function of fiber position. Traditional DAS systems are therefore sensitive to any excitations that create vibrations which stretch/compress the fiber along its axis (i.e. longitudinally).

These systems are however insensitive to acoustic energy that is not parallel to the axis of the optical fiber. Methods that allow for determination of acoustic energy in nonlongitudinal orientations to the optical fiber are of interest to those who practice in the art.

BRIEF DESCRIPTION

Disclosed herein is a method of measuring acoustic energy impinging upon a cable. The method includes, interrogating at least one optical fiber of the cable with electromagnetic energy, the at least one optical fiber is nonconcentrically surrounded by and strain locked to a sheath of the cable, monitoring electromagnetic energy returned in the at least one optical fiber, and determining acoustic energy impinging on the cable.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Embodiments of fiber optic cables disclosed herein employ nonconcentric (i.e. off center) mechanical coupling (strain locking) of optical fiber within cables. This nonconcentric coupling allows sensing of both longitudinal and transverse (bending) deformations of the cables, since all deformations in the cable are directly couple to longitudinal changes in fiber length.

Figure 1:
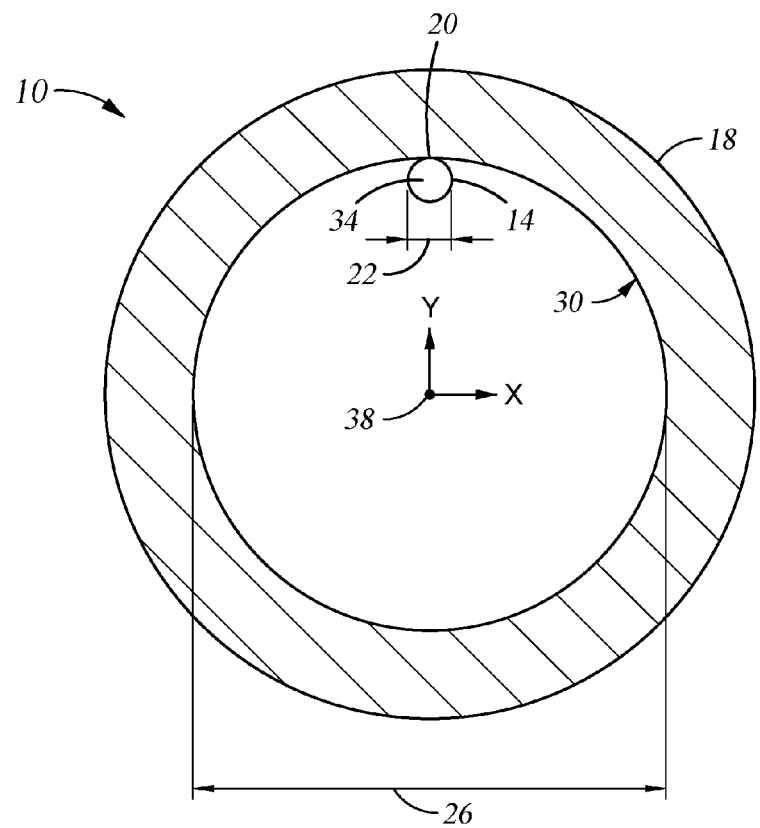
FIG. 1 depicts a cross sectional view of a fiber optic cable disclose herein.

Referring to FIG. 1, an embodiment of a fiber optic cable disclose herein is illustrated in cross section at 10. The fiber optic cable 10 includes, at least one optical fiber 14, with just one being shown in this embodiment, and a sheath 18 surrounding the optical fiber 14. The optical fiber 14 is strain locked to the sheath 18 nonconcentrically such as by an adhesive 20. In this embodiment the optical fiber 14 is sized such that its radial dimension 22 is about or less than one tenth of an inner radial dimension 26 defined by walls 30 of the sheath 18, although any difference in the dimensions 22 and 26 assures that the optical fiber 14 will be strain locked nonconcentrically to the sheath 18 as long as an axis 34 of the optical fiber 14 is not coaxial with a longitudinal axis 38 of the sheath 18.

In the fiber optic cable 10 the axis 34 is parallel to the axis 38 while being offset therefrom. The cable 10 is configured to determine strain exhibited both axially as well as strain created by bending of the cable 10 about an X axis. However, when the cable 10 is bent about a Y axis strain in the sheath 18 may not be readily determined by the optical fiber 14. Additionally, while both axial strain in the cable 10 and strain due to bending of the cable 10 about the X axis are sensible by the optical fiber 14, the sensed strain cannot be readily separated into what portion is due to axial loading and what portion is due to the bending.

Figure 2:
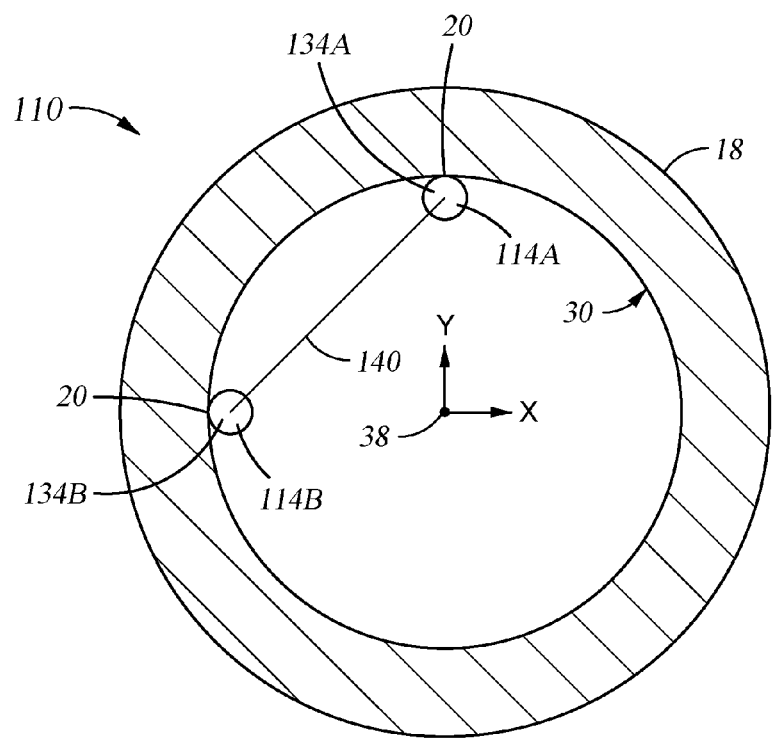
FIG. 2 depicts a cross sectional view of an alternate embodiment of a fiber optic cable disclosed herein.

Referring to FIG. 2, another embodiment of a fiber optic cable disclosed herein is illustrated in cross section at 110. The fiber optic cable 110 has some similarities to the cable 10, as such like elements are numbered with the same reference characters and only the differences are elaborated on hereunder. The cable 110 differs from the cable 10 in the use of two optical fibers 114A, 114B instead of just one. The optical fibers 114A and 114B are oriented about 90 degrees apart, and both are strain locked nonconcentrically to the walls 30 of the sheath 18 such as by the adhesive 20. In one embodiment, axis 134A of the fiber 114A and axis 134B of the fiber 114B are both parallel to the axis 38 of the sheath 18. The foregoing structure allows the cable 110 to sense axial strain as well as bending induced strain in all possible orientations. While all orientations of bending induced strain are sensible there are a few orientations of bending that will produce similar sensed values in the fibers 114A, 114B. These include bending the cable 110 about a 45 degree angle relative to the X and Y axis either toward or away from a plane 140 connecting the axis 134A and 134B.

Figure 3:
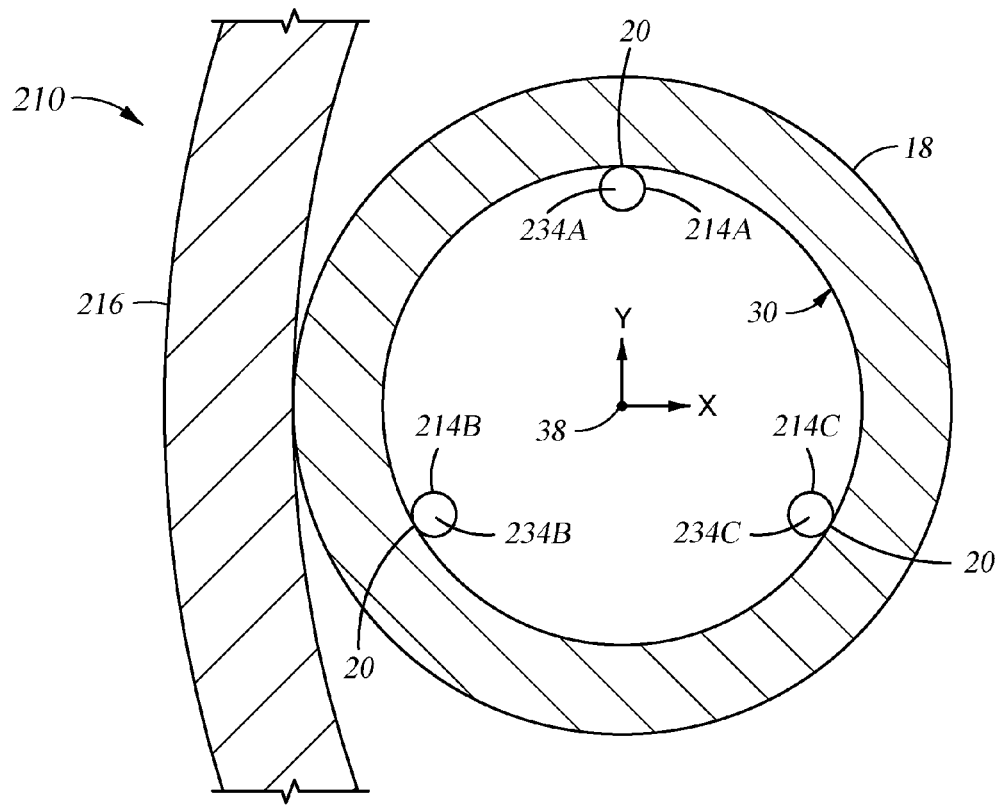
FIG. 3 depicts a cross sectional view of another alternate embodiment of a fiber optic cable disclosed herein.

Referring to FIG. 3, another embodiment of a fiber optic cable disclosed herein is illustrated in cross section at 210. The fiber optic cable 210 has some similarities to the cables 10 and 110, as such like elements are numbered with the same reference characters and only the differences are elaborated on hereunder. The cable 210 includes three optical fibers 214A, 214B and 214C. The optical fibers 214A, 214B and 214C are oriented about 120 degrees from one another, and all three are strain locked nonconcentrically to the walls 30 of the sheath 18 such as by the adhesive 20. In one embodiment axis 234A of the fiber 214A and axis 234B of the fiber 214B and axis 234C of fiber 214C are parallel to the axis 38 of the sheath 18. The foregoing structure allows the cable 210 to sense axial strain as well as bending induced strain in all possible orientations. This sensing also allows separation of axial strain in the cable 210 from bending strain as well as discernment of direction of the bending strain relative to the X and Y axis of the cable 210. This allows for determination of displacement in directions other than parallel to the axis 38 including directions orthogonal to the axis 38.

Figure 4:
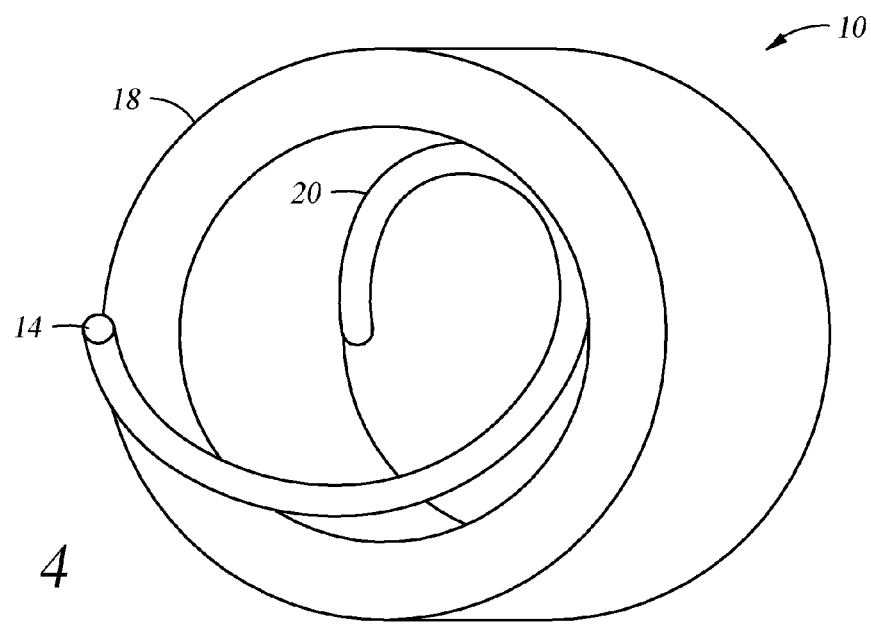
FIG. 4 depicts a partial perspective view of the fiber optic cable of FIG. 1.

It should be noted that other embodiments contemplated could have the optical fibers 14, 114A, 114B, 214A, 214B, 214C of any of the cables 10, 110, 210 oriented in a helical or spiral pattern relative to the sheath 18. One example is shown in FIG. 4 as an embodiment of the cable 10, wherein the optical fiber 14 is attached to the sheath 18 in a helical pattern. Such a configuration causes bending of the cable 10, 110, 210 to impart a longitudinal strain to the fibers 14, 114A, 114B, 214A, 214B, 214C since the fibers 14, 114A, 114B, 214A, 214B, 214C are not displaced from the axis 38 of the sheath 18 in a constant direction. Decreasing a pitch of the helical pattern can allow for increases in spatial resolution of measurements sensed along the cable 10, 110, 210.

The cables 10, 110, 210 disclosed herein, with the mechanical coupling of the optical fibers 14, 114A, 114B, 214A, 214B, 214C to the sheath 18 allow both longitudinal and orthogonal or transverse (bending) deformations of the cable to directly couple to longitudinal changes in fiber length. This contrasts with cable designs in which the fiber is not mechanically coupled to the cable or is coupled but in a concentric way.

The fibers 14, 114A, 114B, 214A, 214B, 214C being mechanically coupled (strain locked) to the cable 10, 110, 210 experience the same strain profile as the cable 10, 110, 210 when it is under mechanical deformation. If properly placed in the cable 10, 110, 210 cross section, localized strain measurements derived from one or more of the mechanically coupled fibers 14, 114A, 114B, 214A, 214B, 214C can therefore be used to reconstruct the cable 10, 110, 210 deformation. Longitudinal stretching/compression as well as magnitude and direction of orthogonal or transverse/bending deformations can be determined locally along the cable 10, 110, 210. Local measurements of the full vibration profile of the cable can be calculated at regular intervals along the cable, yielding a distributed acoustic sensor that is sensitive to vibrations in all directions.

The fiber optic cables 10, 110, 210 disclosed herein are employable in distributed acoustic sensing systems used in earth formation boreholes in the hydrocarbon recovery and carbon dioxide sequestration industries. The cables 10, 110, 210 can be attached to a downhole tool 216 (shown in FIG. 3 only) such as a drillstring, casing or liner, for example, to provide a well operator with static strain measurements of the tool 216 in addition to acoustic and vibration measurements available, whether the tool 216 is stationary or in motion. These measurements include longitudinal as well as nonlongitudinal directions and even directions orthogonal to the axis 38.

Methods of distributed acoustic sensing (DAS) disclosed herein employ the optical cables 10, 110, 210 with the optical fibers 14, 114A, 114B, 214A, 214B, 214C strain locked within the protective metal sheath 18 such that strain on the sheath is transferred effectively to the fiber 14, 114A, 114B, 214A, 214B, 214C. There are several ways to interrogate the fibers 14, 114A, 114B, 214A, 214B, 214C to extract the acoustic signal data as will be discussed hereunder.

For fine spatial resolution, an optical frequency domain reflectometer (OFDR) might be used. In this case, a laser wavelength is swept between 2 wavelengths $\lambda s$ and $\lambda f$ such that $\Delta\lambda = \lambda f - \lambda s$. Then, spacing of points (the smallest possible spatial resolution) is $\Delta z = \lambda s \lambda f / 2 n \Delta\lambda$. So, for example an OFDR sweeping between 1520 and 1560 nm to interrogate a fiber of index n=1.46 would have a spatial resolution of 20.3 um. Such a system could easily interrogate FBG (fiber Bragg grating) sensors spaced millimeters to meters apart, but the maximum length one could interrogate in a sweep is given by sampling theory to be $L_{max}=(Rs\lambda s^2)/(4 n\, d\lambda/dt)$ and the number of data points taken is $N_{max}=Rs\Delta\lambda/(d\lambda/dt)$ where Rs is the sampling rate and $d\lambda/dt$ is the laser sweep rate. The sweep time is given by $\Delta t = \Delta\lambda/(d\lambda/dt)$. So, for example to interrogate a 1 km fiber using OFDR swept from 1520 to 1560 nm one could choose a sweep rate of 100 nm/s which would require a fast sampling rate Rs of 253 MHz. Then the number of data points would be 101 million and the time to sweep would be 0.4 s. One concern with this interrogation approach is the huge data set which must be processed to strain data and acoustic data and the slow speed. Taking data for 0.4 s would limit the time response to a little more than 1 Hz, which is a bit slow for a meaningful DAS system. So, the sweep range should be decreased or the sweep rate increased for DAS, thus limiting either the distance or requiring a very fast sampling rate. For example, to achieve a 500 Hz DAS system, interrogation time might be limited to 0.1 ms. A laser might be swept at 10,000 nm/s, a very fast rate for a laser. The scan range would then only be 10 nm, and achieving a 1 km interrogated length would require a 25 GHz sampling rate. So, balancing is needed between length and speed of a DAS system using OFDR due to the speed of electronics employed to process the data.

The design of an OFDR system and the configuration of the cable 10, 110, 210 as described above are intimately related. So, the cable 10 as described above with the single optical fiber 14 strain locked in a helical pattern with several FBGs per helical period might be interrogated using OFDR for this purpose. For example, the fiber 10 might be helixed at a period of 16 cm (about 6 rotations per m) with FBGs spaced 2 cm apart (8 per helix), providing a spatial resolution of sensing of about 16 cm, being able to distinguish between longitudinal and transverse (orthogonal to the axis 38) acoustic waves on this scale, and being able to detect any type of acoustic wave on a 2 cm spatial scale. It would also be possible to use the cable 210 with the three fibers 214A, 214B, 214C with FBGs 2 cm apart at 120 degree relative orientation, not helixed. All three of the fibers 214A, 214B, 214C could be interrogated and provide 2 cm three-dimensional spatial resolution of a DAS signal based on this FBG spacing. The same system could utilize Rayleigh scattering rather than FBGs, providing a weaker signal but a much finer spatial resolution, determined as above by the sweep range of the laser. So, several configurations of sensors according to the embodiments described above could be interrogated by different OFDR systems to provide three-dimensional spatial resolution from a few microns to a few meters and interrogation lengths from a few meters to hundreds of meters, according to the equations above. All could take advantage of the unique characteristics of the cables 10, 110, 210 described.

A courser spatial resolution but much longer system length might be provided by a Coherent Optical Time Domain Reflectometer (CoOTDR) which is another embodiment for interrogating a DAS system disclosed herein. A narrow linewidth (coherent) source is pulsed and sent through the fiber 10, 110, 210, causing interference that is a function of time. Time of flight determines what section of the fiber is interrogated at each time. A 10 ns pulse can produce a 1 m spatial resolution in a typical fiber and the pattern that returns is a complex function of the acoustic waves impinging on the fiber 10, 110, 210. It is possible to extract the location (to within typically 1 m) and frequency content (to a few hundred Hz) of acoustic waves impinging on a many km fiber as long as the signal caused by Rayleigh scatter is strong enough to overcome signal to noise limitations. Hence, a CoOTDR based system could operate to interrogate a cable as described. A helical cable would not be useful unless the spatial period of the helix was greater than the spatial resolution of the CoOTDR system. However, the multifiber cables 110, 210 could be used to allow spatial resolution to match the spatial resolution of the CoOTDR system, typically about 1 m. If the cable 110, 210 was strain locked, and the multiple fibers 114A, 114B, 214A, 214B, 214C were interrogated, the cables 110, 210 as described above would be advantageous for the reasons described above.

Another embodiment of a method of interrogation is to use wavelength division multiplexed (WDM) sensors. As long as only a countable finite number of sensors is needed, it would be possible to make each sensor an FBG at a different wavelength and interrogate each in its wavelength range.

Any number of hybrid systems, combining features of those described above or other similar techniques for discerning time varying strain signals can benefit from the use of the cables 10, 110, 210 disclosed herein. The signals can be used to determine magnitudes of acoustic wave, acoustic spectrum (to identify what type of thing created the wave), and phase (to identify direction the wave is traveling), for example. In some cases, acoustic energy is generated at a known location and then measurements are made downhole with the cables 10, 110, 210 to image the space between the source and the cables 10, 110, 210. The measurements includes determining a disturbance in a reflected signal as a function of time (either phase, amplitude or both), which is processed to determine some characteristic of the acoustic wave (location, strength, direction of travel, image of what it passed through, etc). The presence of the fibers 14, 114A, 114B, 214A, 214B, 214C at a distance from the longitudinal axis 38 makes the measurement more sensitive to transverse traveling acoustic waves.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of measuring acoustic energy impinging upon a cable, comprising:
   interrogating at least one optical fiber of the cable with electromagnetic energy, the at least one optical fiber being nonconcentrically surrounded by and strain locked to a sheath of the cable;
   monitoring electromagnetic energy returned in the at least one optical fiber; and
   determining acoustic energy impinging on the cable.

2. The method of measuring acoustic energy impinging upon a cable of claim 1, wherein the interrogating includes sweeping a laser between two wavelengths.

3. The method of measuring acoustic energy impinging upon a cable of claim 2, further comprising sweeping the laser between wavelengths of about 1520 nm and 1560 nm.

4. The method of measuring acoustic energy impinging upon a cable of claim 2, further comprising sweeping the laser at a rate of between about 100 nm/s and 10,000 nm/s.

5. The method of measuring acoustic energy impinging upon a cable of claim 1, further comprising interrogating lengths of the at least one optical fiber of few meters to hundreds of meters.

6. The method of measuring acoustic energy impinging upon a cable of claim 1, further comprising interrogating fiber Bragg grating sensors.

7. The method of measuring acoustic energy impinging upon a cable of claim 1, further comprising interrogating an optical frequency domain reflectometer.

8. The method of measuring acoustic energy impinging upon a cable of claim 1, further comprising monitoring electromagnetic energy returning from Rayleigh scatterings.

9. The method of measuring acoustic energy impinging upon a cable of claim 1, further comprising interrogating with coherent optical time domain reflectometer.

10. The method of measuring acoustic energy impinging upon a cable of claim 9, further comprising interrogating with pulses of electromagnetic energy.

11. The method of measuring acoustic energy impinging upon a cable of claim 1, further comprising interrogating with wavelength division multiplexed sensors.

12. The method of measuring acoustic energy impinging upon a cable of claim 1, further comprising determining time varying displacement of the cable while the cable is strain locked to a tool.

13. The method of measuring acoustic energy impinging upon a cable of claim 1, further comprising determining acoustically induced displacements in three-dimensions at distributed points on the cable.

14. The method of measuring acoustic energy impinging upon a cable of claim 1, further comprising determining parameters of acoustic energy impinging the cable in directions not parallel to a longitudinal axis of the cable.

15. The method of measuring acoustic energy impinging upon a cable of claim 14, wherein the parameters include at least one of acoustic spectrum, phase, and amplitude of the acoustic energy.

16. The method of measuring acoustic energy impinging upon a cable of claim 14, wherein the parameters includes a location of a source of the acoustic energy.

17. A method of measuring acoustic energy impinging upon a cable, comprising:
   interrogating at least one optical fiber of the cable with electromagnetic energy, the at least one optical fiber being nonconcentrically surrounded by and strain locked to a sheath of the cable;
   monitoring electromagnetic energy returned in the at least one optical fiber; and
   determining acoustic energy impinging on the cable determining parameters of acoustic energy impinging the cable in directions not parallel to a longitudinal axis of the cable wherein the parameters includes a direction of travel of the acoustic energy.

18. A method of measuring acoustic energy impinging upon a cable, comprising:

interrogating at least one optical fiber of the cable with electromagnetic energy, the at least one optical fiber being nonconcentrically surrounded by and strain locked to a sheath of the cable;

monitoring electromagnetic energy returned in the at least one optical fiber; and determining acoustic energy impinging on the cable; and determining parameters of acoustic energy impinging the cable in directions not parallel to a longitudinal axis of the cable wherein the parameters includes an image of what the acoustic energy has passed through.

19. The method of measuring acoustic energy impinging upon a cable of claim 14, wherein the at least one optical fiber is positioned within the sheath in a helical pattern.

\* \* \* \* \*